United States Patent
White et al.

(10) Patent No.: US 9,588,041 B2
(45) Date of Patent: Mar. 7, 2017

(54) SYSTEM AND METHOD FOR DETECTION AND MEASUREMENT OF INTERFACIAL PROPERTIES IN SINGLE AND MULTILAYER OBJECTS

(75) Inventors: Jeffrey S. White, Manchester, MI (US); Gregory D. Fichter, Ann Arbor, MI (US); Irl Duling, Ann Arbor, MI (US); David Zimdars, Ann Arbor, MI (US)

(73) Assignee: PICOMETRIX, LLC, Ann Arbor, MI (US)

( * ) Notice: Subject to any disclaimer, the term of this patent is extended or adjusted under 35 U.S.C. 154(b) by 263 days.

(21) Appl. No.: 13/501,250

(22) PCT Filed: Oct. 13, 2010

(86) PCT No.: PCT/US2010/052467
§ 371 (c)(1), (2), (4) Date: Aug. 7, 2012

(87) PCT Pub. No.: WO2011/047016
PCT Pub. Date: Apr. 21, 2011

(65) Prior Publication Data
US 2012/0304756 A1 Dec. 6, 2012

Related U.S. Application Data

(60) Provisional application No. 61/250,983, filed on Oct. 13, 2009.

(51) Int. Cl.
*G01N 29/04* (2006.01)
*G01N 29/11* (2006.01)
(Continued)

(52) U.S. Cl.
CPC ......... *G01N 21/3586* (2013.01); *G01N 29/04* (2013.01); *G01N 29/11* (2013.01); (Continued)

(58) Field of Classification Search
USPC .. 73/150 A, 150 R, 582, 588, 573, 594, 579, 73/800, 801, 788
See application file for complete search history.

(56) References Cited

U.S. PATENT DOCUMENTS 3,605,486 A * 9/1971 Anderholm et al. ........... 73/788
3,825,819 A * 7/1974 Hansen et al. .............. 73/150 A
(Continued)

FOREIGN PATENT DOCUMENTS

JP 2009075069 4/2009

OTHER PUBLICATIONS

Japanese Office Action and translation of same dated Jan. 7, 2014.

*Primary Examiner* — Helen Kwok
(74) *Attorney, Agent, or Firm* — Brinks Gilson & Lione

(57) ABSTRACT

A system for determining a material property at an interface between a first layer and a second layer includes a transmitter outputting electromagnetic radiation to the sample, a receiver receiving electromagnetic radiation that was reflected by or transmitted though the sample, and a data acquisition device. The data acquisition device digitizes the electromagnetic radiation to yield waveform data. The waveform data represents the radiation reflected by or transmitted though the sample. The material property to be determined is generally the adhesive strength between the first and second layers.

31 Claims, 7 Drawing Sheets

(51) Int. Cl.
  *G01N 29/48* (2006.01)
  *G01N 21/3586* (2014.01)
  *G01N 19/04* (2006.01)
  *G01N 21/3581* (2014.01)

(52) U.S. Cl.
  CPC ............ *G01N 29/48* (2013.01); *G01N 19/04* (2013.01); *G01N 21/3581* (2013.01)

(56) References Cited

U.S. PATENT DOCUMENTS

| | | | |
|---|---|---|---|
| 4,004,456 A * | 1/1977 | Vahaviolos | 73/801 |
| 4,100,808 A * | 7/1978 | Evans et al. | 73/588 |
| 4,137,991 A * | 2/1979 | Melcher et al. | 181/142 |
| 4,255,971 A * | 3/1981 | Rosencwaig | 73/606 |
| 4,513,384 A * | 4/1985 | Rosencwaig | 702/170 |
| 4,875,175 A * | 10/1989 | Egee et al. | 702/30 |
| 4,934,191 A * | 6/1990 | Kroening et al. | 73/592 |
| 4,944,185 A * | 7/1990 | Clark et al. | 73/579 |
| 5,088,327 A * | 2/1992 | Gammell | 73/588 |
| 5,107,709 A * | 4/1992 | McCarty | 73/655 |
| 5,438,402 A * | 8/1995 | Gupta | 356/35.5 |
| 5,537,876 A * | 7/1996 | Davidson et al. | 73/624 |
| 5,748,318 A | 5/1998 | Maris et al. | |
| 6,069,703 A * | 5/2000 | Banet et al. | 356/432 |
| 6,613,169 B2 * | 9/2003 | Georgeson et al. | 156/64 |
| 6,795,198 B1 * | 9/2004 | Fuchs et al. | 356/521 |
| 7,204,146 B2 * | 4/2007 | Ishimaru et al. | 73/579 |
| 7,341,758 B2 * | 3/2008 | Stewart et al. | 427/8 |
| 7,449,695 B2 | 11/2008 | Zimdars et al. | |
| 7,507,312 B2 * | 3/2009 | Bossi et al. | 156/714 |
| 7,509,876 B1 * | 3/2009 | Sokol et al. | 73/827 |
| 7,765,861 B2 | 8/2010 | Jacquemin | |
| 8,132,460 B1 * | 3/2012 | Toller et al. | 73/588 |
| 8,225,664 B1 * | 7/2012 | Sokol et al. | 73/588 |
| 8,457,915 B2 | 6/2013 | White et al. | |

\* cited by examiner

SYSTEM AND METHOD FOR DETECTION AND MEASUREMENT OF INTERFACIAL PROPERTIES IN SINGLE AND MULTILAYER OBJECTS

CROSS REFERENCE TO RELATED APPLICATIONS

This application claims priority to PCT/US2010/052467, filed on Oct. 13, 2010, which claims benefit of U.S. Provisional Application No. 62/250,983, filed on Oct. 13, 2009.

BACKGROUND

The present invention relates to systems and methods to measure material properties using electromagnetic radiation. Electromagnetic radiation is potentially useful in many industrial measurement applications. The data acquisition of reflected and/or transmitted radiation off and/or through a sample can be used to determine several material properties. For example, electromagnetic radiation has been used to determine if the sample is an explosive device, such as commonly found in airport and seaport scanning systems.

However, electromagnetic radiation has not been used to determine if layers of a multilayer sample are appropriately adhered to one another. Further, other than destructive testing, it is extremely difficult to determine the adhesion between layers of a multilayer sample. Therefore, there is a need for a nondestructive testing and analysis system to determine the adhesion strength between layers of a multilayer sample.

SUMMARY

A system and method for determining a material property at an interface between a first layer and a second layer of a sample is described. The system includes a transmitter outputting electromagnetic radiation to the sample, a receiver receiving electromagnetic radiation that was reflected by or transmitted though the sample, and a data acquisition device. The data acquisition device is configured to digitize the electromagnetic radiation reflected by or transmitted though the sample to yield waveform data, wherein the waveform data represents the radiation reflected by or transmitted though the sample, the waveform data having a first magnitude, a second magnitude and a third magnitude.

The first magnitude represents a reflected or transmitted portion of the electromagnetic radiation provided to a top surface interface of the first layer. The second magnitude represents a reflected or transmitted portion of the electromagnetic radiation provided to the interface between the first and second layers, and the third magnitude represents a reflected or transmitted portion of the electromagnetic radiation provided to a bottom surface interface of the second layer. Thereafter, the data acquisition device configured to determine a material property between the first layer and the second layer of the sample by analyzing the second magnitude and/or third magnitude. Generally, the material property to be determined is adhesive strength between the first and second layers.

The data acquisition device is further configured to determine the adhesive strength between the first layer and the second layer of the sample by comparing the second magnitude to a reference magnitude. The data acquisition device is further configured to determine the adhesive strength between the first layer and the second layer of the sample by comparing the third magnitude to a reference magnitude. Finally, the data acquisition device is may be further configured to determine the adhesive strength between the first layer and the second layer of the sample by comparing the third magnitude to the second magnitude.

Additionally, the data acquisition device may be further configured to determine an adhesive strength between the first layer and the second layer of the sample by analyzing the waveform data to determine if a fourth magnitude is located between the third magnitude and the second magnitude in time. The data acquisition device may determine that there is reduced adhesive strength between the first layer and the second layer when a fourth magnitude is located between the third magnitude and the second magnitude in time.

As to the electromagnetic radiation utilized, the electromagnetic may be terahertz radiation, either continuous wave or time domain terahertz radiation, in the 25 GHz to 10 THz frequency. However types of electromagnetic radiation may be utilized.

DETAILED DESCRIPTION

Figure 1A:
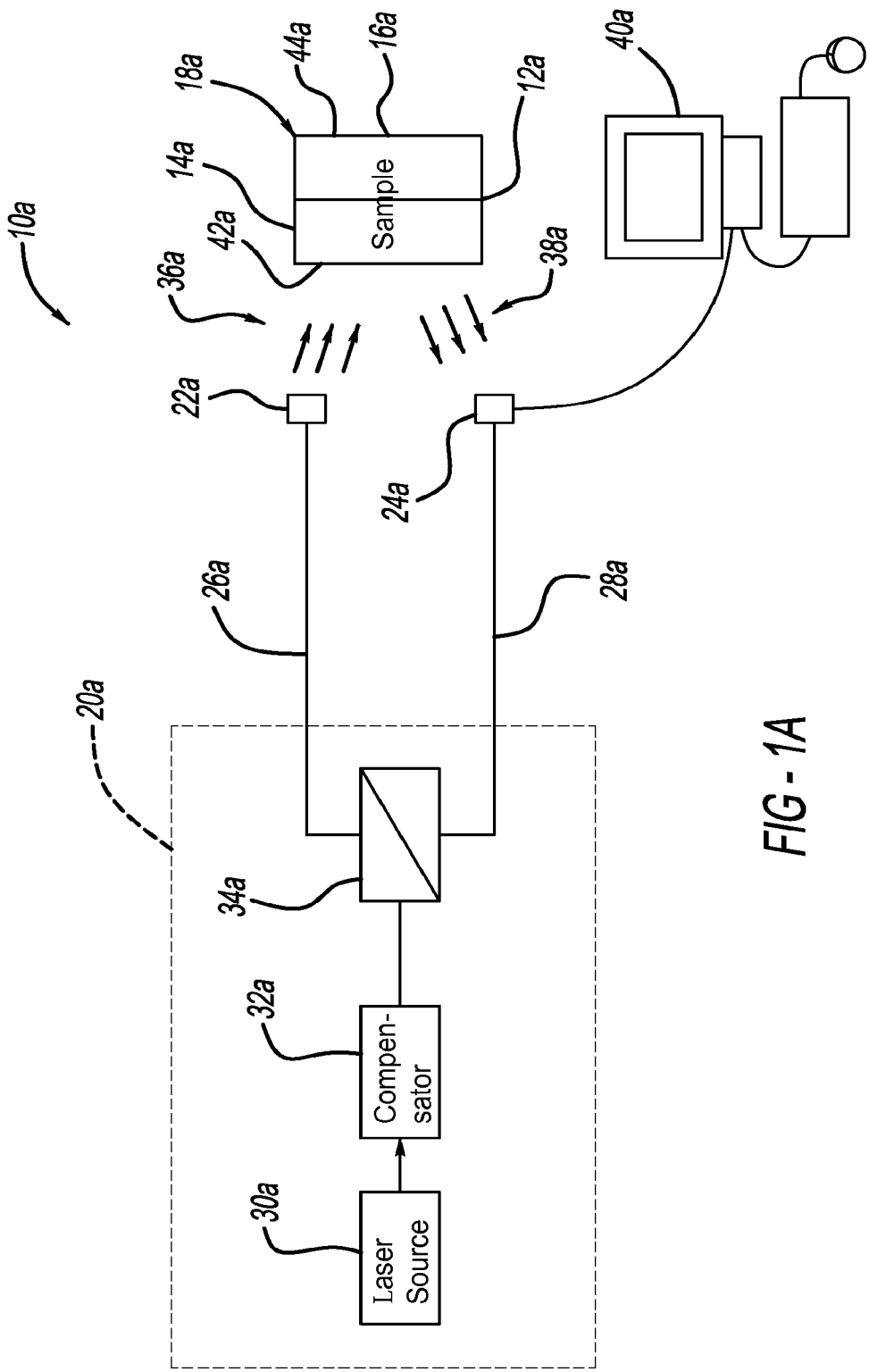
FIG. 1A illustrates a system to determine the material properties between two layers of a sample using reflected electromagnetic radiation.

Referring to FIG. 1A, a system 10a for determining a material property at an interface 12a between a first layer 14a and a second layer 16a of a sample 18a is shown. As its primary components, the system 10a includes an optical control source 20a, an electromagnetic radiation transmitter 22a, an electromagnetic radiation receiver 24a and a means 26a and 28a for providing optical signals outputted by the optical control source 20a to both the transmitter 22a and a receiver 24a. The means 26a and 28a for providing the optical signal is such that the receiver 24a is synchronized to the transmitter 22a by optical signals emitted by the optical control source 20a. In this embodiment, the means 26a and 28a are single mode optical fibers. However, the means 26a and 28a may be multi mode fibers or even a free space transmission of the optical signals from the optical control source 20a to the transmitter 22a and/or the receiver 24a.

Generally, the optical control source 20a may take a variety of different forms. In one such embodiment, the optical control source 20a includes a laser source 30a configured to output optical pulses. Generally, the laser source 30a produces femtosecond output pulses. Optically coupled to the laser source 30a is a compensator 32a. Optical pulses emitted by the laser source 30a are provided to the compensator 32a which adds opposite sign dispersion to the optical pulses to correct for a stretching of the optical pulses as they travel through the means 26a and 28a when the means 26a and 28a are optical fibers. In a free space transmission of the optical pulses to the transmitter 22a and the receiver 24a, the compensator 32a is generally unnecessary and can be omitted. The compensator 32a and laser source 30a may be optically coupled to each other by an optical fiber or may be optically coupled to each other in a free space manner.

Once the appropriate amount of opposite sign dispersion is provided to the optical pulses by the compensator 32a, the optical pulses are provided to a splitter 34a. The splitter 34a splits the optical pulses and provides them to a first optical fiber 26a and a second optical fiber 28a. In this embodiment, the first optical fiber 26a is a single mode fiber wherein pulses split by the splitter 34a are provided to the optical fiber 26a. In like matter, the second optical fiber 28a is also an optical fiber receiving pulses split from the splitter 34a.

The optical fiber 24a is coupled to the transmitter 22a. Similarly, optical fiber 26a is optically coupled to receiver 24a. When the receiver 22a receives these optical pulses from the optical fiber 26a, the receiver 22a will output radiation 36a to a sample 18a. When the receiver 24a receives optical pulses from the optical fiber 28a, the receiver 24a will receive the radiation 38a emitted from the transmitter 22a and reflected off the sample 18a. Because of this, timing is incredibly important such that the receiver 24a is synchronized to the transmitter 22a by the optical pulses traveling on optical fiber 26a and optical fiber 28a.

Once the radiation 38a is received by the receiver 24a, the receiver 24a generates an electrical signal which can be interpreted, scaled and/or digitized by a data acquisition system 40a. The data acquisition system 40a is generally electrically coupled to the receiver 24a so as to receive the electrical signals from the receiver 24a.

Figure 1B:
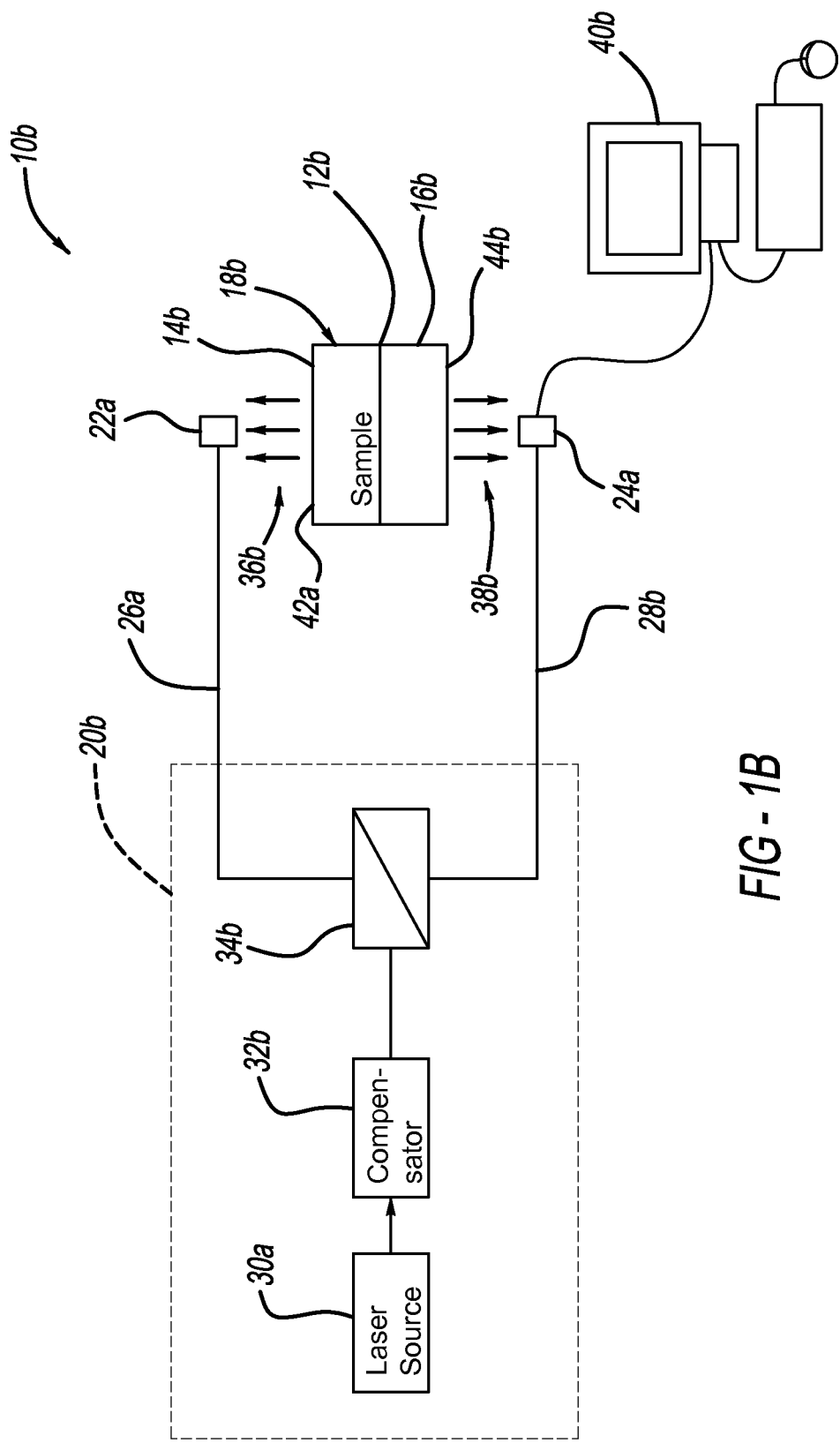
FIG. 1B illustrates a system to determine the material properties between two layers of a sample using transmitted electromagnetic radiation.

In this embodiment, the radiation 36a is reflected off the sample 18a and sends as this as radiation 38a to the receiver 24a. However, it should be understood that the systems and methods disclosed in this application are equally applicable to transmitted radiation. Moreover, referring to FIG. 1B, disclosed is a system 10b that is similar to system 10a of FIG. 1A. Like reference numerals have been used to denote like components, with the only difference being that the reference numerals have the letter "b" after them in FIG. 1B instead of an "a" after them in FIG. 1A. The system 10b shows the transmitter 22b sending radiation 36b though the sample 18b. This radiation is transmitted though sample 18b and sent to receiver 24b as radiation 38b. Additionally, it should be understood that a system may incorporate the use of both transmitted and reflected radiation in a single system.

Generally, the radiation 36a and 36b emitted from the transmitters 22a and 22b is terahertz radiation having a frequency range of 10 GHz up to 50 THz but is generally has a range of 25 GHz to 10 THz. However, other frequency ranges may be used. Generally, the terahertz radiation utilized will be time-domain terahertz radiation. However this other types of bandwidth sources may be used including continuous wave and discrete bandwidth sources.

The samples 18a and 18b are identical, therefore only sample 18a will be described; however, the same description applies to sample 18b. The sample 18a has a first layer 14a and a second layer 16a. It is also important to note that the sample has a first surface 42a (front surface) and a second surface 44a (back surface) located on opposite sides of the sample 18a. Between the two layers 14a and 16a is an interface 12a. The interface 12a is generally an area of adhesion between the first layer 14a and the second layer 16a.

Once a pulse of time-domain terahertz radiation 36a has interacted with the sample 18a, a number of useful measurements can be extracted from acquired time-domain or transformed spectroscopic domain data. Possible measurements include, but are not limited to, sample mass, thickness, density, refractive index, density and surface variations, and spectroscopy (e.g. moisture content, polymorph identification). In time-domain terahertz, the changes in the terahertz radiation pulses after they have interacted with the sample 18a are typically available as a time-domain waveform, which can be recorded or analyzed to determine other parameters (e.g., pulse signal amplitude)

For example, as the pulse transmits through the sample 18a, the terahertz pulse's arrival at the receiver 24a will attenuated and delayed compared to the transmission of the same pulse through an air path. The amount of the pulse delay is determined by the sample's 18a group refractive index value and the amount of mass in the sampling beam. The attenuation of the pulse is also dependent on the refractive index (Fresnel reflection loss) and the attenuation of the pulse's frequencies of the sample 18a material. Scattering of radiation within the sample 18a will also affect the pulse's amplitude.

Additional measurements can be made with reflections of the time-domain terahertz pulses off a single or multilayer sample object. The systems and methods claimed in this application adds capabilities by measuring and quantifying the physical properties of the interface 12a of the sample 18a and using that information to add more broad classes of property measurement (e.g., interface adhesion or degree of separation).

Electromagnetic radiation will reflect some energy at any interface of differing materials (Fresnel reflection) or material properties (e.g., density change leading to change in dielectric constant and thus refractive index). Thus, reflections from the front/rear surfaces and interfacial surfaces of the sample 18a can be observed. The amplitude of the reflected pulse allows the immediate calculation of material physical properties. For example, the fraction of incident power reflected (typically denoted R) or electric field amplitudes (typically denoted r) can be used to directly calculate the refractive index of a material according to the well established Fresnel equations.

$$R = R_s = R_p = \left(\frac{n_1 - n_2}{n_1 + n_2}\right)^2$$

It can be seen from this equation that the larger the difference between the two materials index of refraction values, the larger the fraction of incident power reflected. For the above equation to be valid, the reflection needs to be at normal incidence. If the refractive index of one of the materials around the interface is known (e.g., air), the measurement of the reflection coefficient off the first surface 42a can be used to directly calculate the refractive index of the unknown material. Additionally, in normal incidence the reflection coefficients of the two polarization states of incident electromagnetic radiation are equal. Measurement at non-normal incidence, leading to non-equal values for reflection coefficients for the two polarization states will be considered later.

For interfaces in multilayer objects, such as the sample 18a, the refractive index of one or both layers 14a and 16a need to be predetermined to obtain an absolute value.

However, there are many instances in which the relative difference of the refractive index values can provide critical information.

An example is the contact between two layers 14a and 16a, either the same or differing materials. If the two layers 14a and 16a are the same and the contact between the layers 14a and 16a is sufficiently intimate, theoretically there will be no energy reflected. This can be visualized as the reverse amplitude pulses for the two interfaces fully interfering and thus cancelling as the layers 14a and 16a are brought into intimate contact. In this case, there is no reflected energy.

However, as the two layers 14a and 16a either separate from each other, or conversely are compressed at the interface 12a, the interstitial area at the layers 14a and 16a interface 12a must change in their dielectric constant/refractive index value. If the refractive indices of the layers 14a and 16a change, the reflection coefficient for this interface 12a will also change. Measurement of the amplitude of the reflected pulse off this interface 12a will reflect the change in the reflection coefficient. Thus, this amplitude can be used to monitor physical and material property changes in the interfacial region.

If the two layers 14a and 16a are initially of differing materials, there would be some reflection coefficient value even with the layers 14a and 16a in intimate contact. The amplitudes of the two interfering reflections will not be the same and thus would not fully cancel. Thus, some residual of the incident energy is reflected at the interface 12a.

Again, as the layers 14a and 16a either separated or are compressed at the interface 12a, the physical properties of the layers 14a and 16a, and that of the interface 12a itself, change. This delta change can be observed and measured from the amplitude of the reflected energy. These delta changes can be observed and measured even without any knowledge of the material on interstitial interface's 12a refractive index value.

Figure 2:
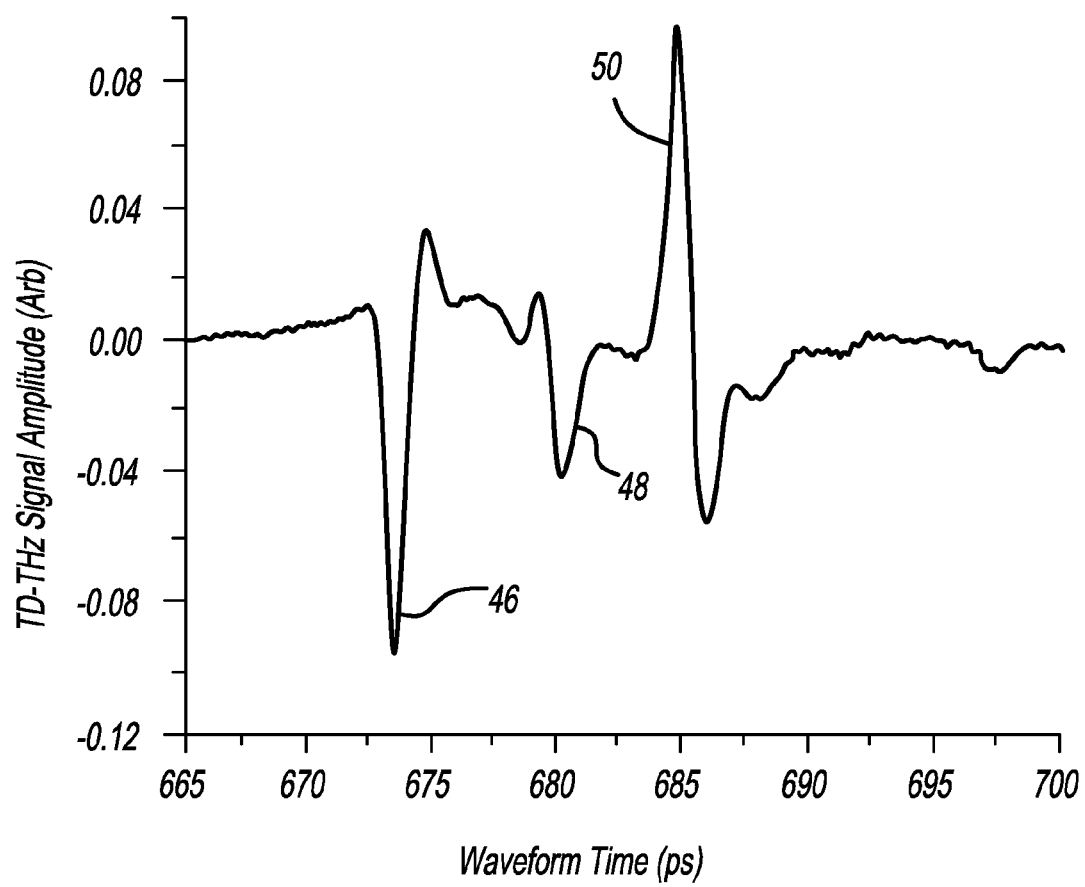
FIG. 2 illustrates a waveform of a two layer sample.

Another example considers when the layers 14a and 16a at the interface 12a are adhered to one another. At the interface 12a there will be two layers 14a and 16a and a delta value in refractive index. With a non-zero delta refractive index value, there will some reflected power. An example time-domain waveform demonstrating this point for the sample 18a is shown in FIG. 2. FIG. 2 shows a first magnitude 46 representing a reflected or transmitted portion of the radiation provided to the first surface 42a, a second magnitude 48 representing a reflected or transmitted portion of the radiation provided to the interface 12a, and a third magnitude 50 representing a reflected or transmitted portion of the radiation provided to the second surface 44a.

For the layers 14a and 16a adhered to one another, the adhesion can vary, up to the point where the layers 14a and 16a become fully separated. For the case of the layers 14a and 16a with some contact and/or adhesion between the layers 14a and 16a, three reflection magnitudes will occur.

In the case of when the layers 14a and 16a are fully separated, additional reflection peak(s) are seen. In a two layer example, there would be four interfaces in the sample; the front and rear surfaces of the first layer 14a and similarly the top and rear surfaces of the second layer 16a. Measurement of the time between the reflection from the rear surface of the first layer 42a and the front surface of the second layer 44a is used the measure the layers' 14a and 16a separation distance. In this example, the $4^{th}$ peak is referred to as an optional peak because it will only appear in the situation when the layers 14a and 16a are fully separated. The detection of layer separation does not require knowledge of physical property values of the two layer's material.

Figure 3:
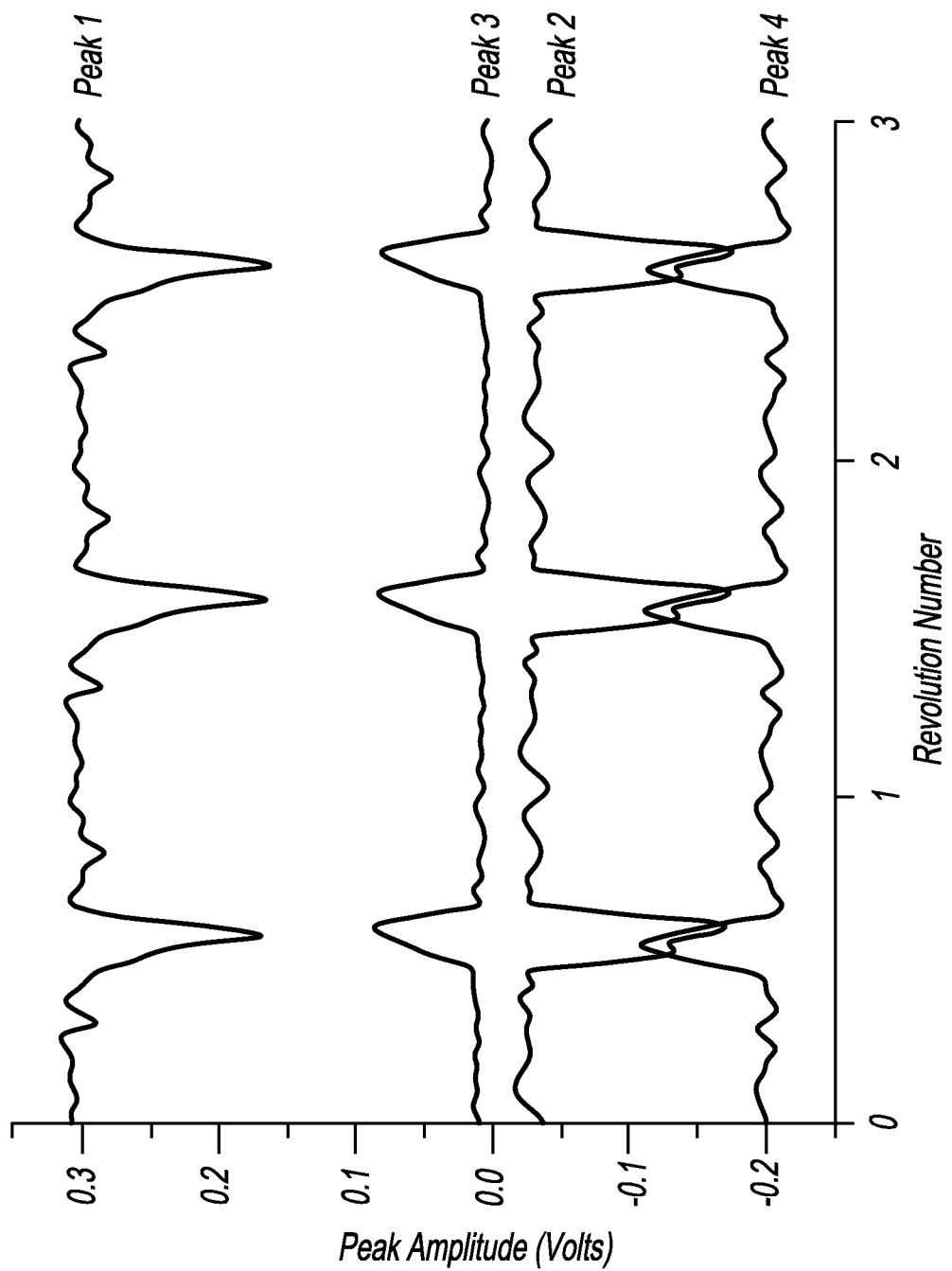
FIG. 3 illustrates the reflection amplitudes for all interface peaks of a sample.

A nominally adhered two layer sample 18a containing a section where the layers are fully separated was measured in reflection. The sample was fabricated in a circular belt so the same positions could be repeatable measured. The reflection amplitudes for all interface peaks found are shown in FIG. 3.

This data represents three revolutions (repeated measurements) of the sample 18a. Four reflection peaks are observed, thus the optional peak is present. This data confirms the capability to measure the partial reflection power off various interface(s) in the multilayer sample 18a and use the measured amplitudes to detect and locate sections of samples with fully separated layers. If there is some adhesion between these layers (low adhesion state), the amplitude of the optional peak(s) will drop below the prescribed level set to indicate the condition of full layer separation.

However, the amplitude of the interface peak will still indicate changes in the interface. Similar to the case of materials in contact, the physical nature of the interface will change as the adhesion between the layers changes.

Possible conditions that could lessen the adhesion between layers are a separation (i.e., pulling) force or to misadjusted manufacturing process. The density of interfacial material could change (reduce in this case) with the introduction of air or partial vacuum in the interstitial space of the interface. This material physical change will lead to a density change and subsequently affect the refractive index of the interface materials. In particular, the delta refractive index value will change.

A two layer sample, with a purposefully introduce defect region with no/low adhesion between the layers, was probed in to measure the amplitude of the electromagnetic energy reflected at the interface. The amplitude of the interfacial reflection peaks are plotted in FIG. 4.

Figure 4:
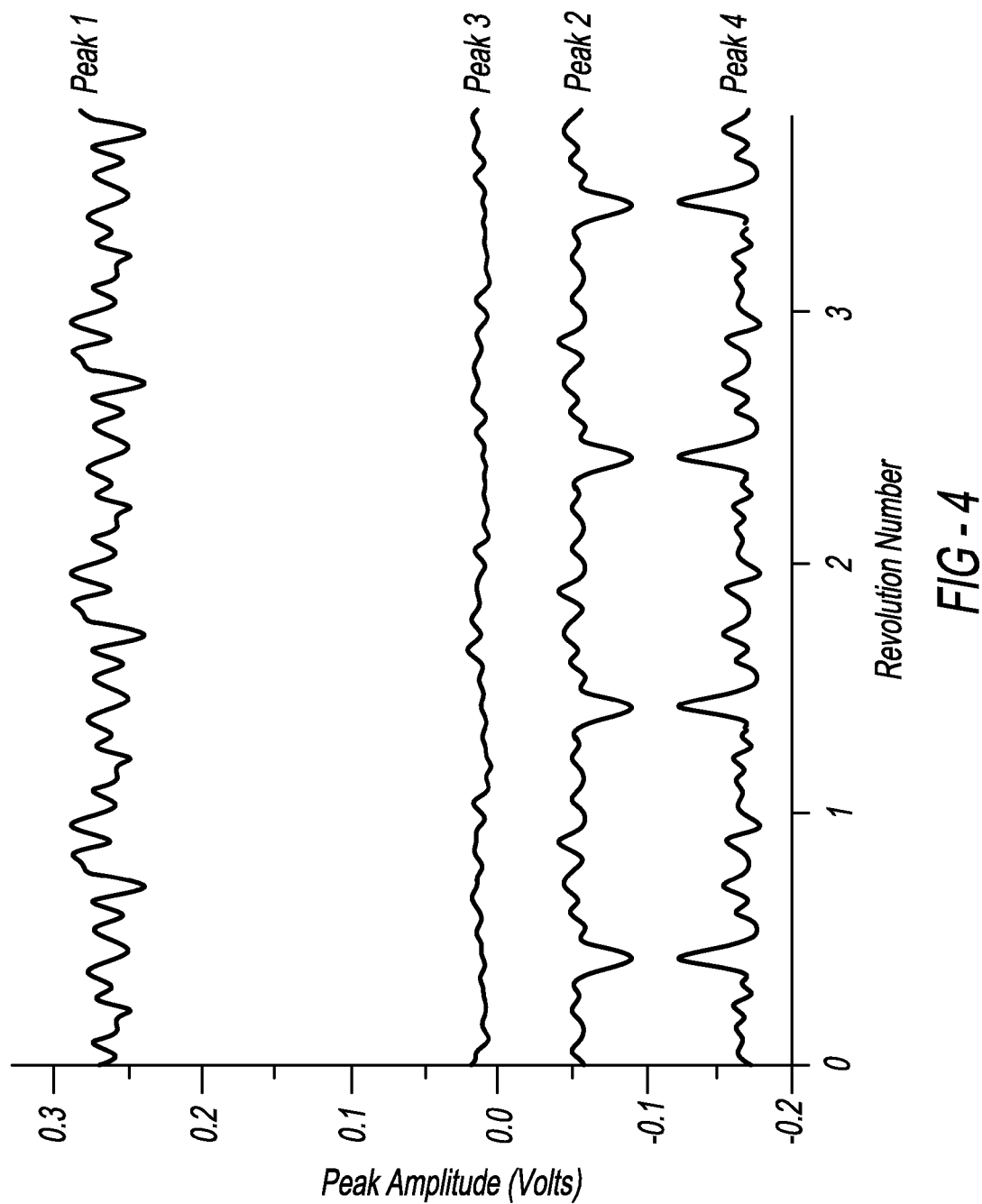
FIG. 4 illustrates the amplitude of the interfacial reflection peaks of a sample.

Referring to FIG. 4, in this data, there were 4 repetitions of the defect region. Note that the optional peak (Peak 3 in FIG. 4) is now essentially zero. Therefore, at least some adhesion between the layers exists. Yet the repeated changes in the reflection power of the interface 12a (Peak 2), and second surface 44a (Peak 4), reflection correspond to the low adhesion section of the sample. The reflection amplitude increases (become more negative in this case) at the defect regions. The amplitude of this peak can be correlated to the adhesion of the interface.

Also notice that the amplitude of Peak 4, which corresponds to the sample rear surface/air interface, changes (reduces) in the defect regions. This is expected. Subsequent interfacial reflections will change, with the opposite magnitude, at the spatial positions that an upper interface reflection coefficient changes. In this case, the low adhesion at the interface will result in a greater delta refractive index at the interface. The low adhesion will permit air/partial vacuum to exist at the interface 12a which will result in a larger refractive index change at the interface. This will result in a larger percentage of the incident energy being reflected at the interface 12a. Therefore, there will be less incident energy on all subsequent interfaces. In this example, the reflected energy from the second surface 44a is reduced. The increase in an interface reflection coefficient with a concomitant reduction in subsequent interface reflection coefficient is a powerful indication of changes in the interface properties.

It is possible to have the interfacial property change result in a reduction of the interfacial reflection energy. If the change in the material's physical property, e.g., density, results in a smoother transition of refractive index between the two materials, then a reduction of the reflection energy would occur. This would then lead to an increase in the reflection energy form subsequent interfaces. In the limit of a smooth transition between materials, the reflection coefficient at the interface in question could become zero. A similar process can occur with stacks of precise thickness, refractive index coating (i.e., anti-reflection coatings).

The combination of monitoring the amplitude of both an interface and the subsequent interface(s) reflection characteristics can provide a more sensitive measure of interface properties (e.g., low adhesion). An example calculation is the ratio of the reflection peak amplitude of the interface of interest ($Pk_n$) to the reflection peak amplitude of the next interface ($Pk_{n+1}$).

$$Factor \propto A_{Pkn}/A_{Pkn+1}$$

In the adhesion example considered here, we would like this factor to indicate the adhesion between two layers 14a and 16a. The value above relationship would decrease as the adhesion increases. A preferred method would have the factor increase as the adhesion increases. Thus an "Adhesion Factor", to indicate a positive correlation to the adhesion between two layers 14a and 16a, is defined to be:

$$Adhesion\ Factor = 1/(A_{Pkn}/A_{Pkn+1}) = A_{Pkn+1}/A_{Pkn}$$

This factor was used to study a two layer sample 18a during manufacture. A defect was purposefully introduced into the continuously manufactured sample. The fully separated defect was immediately generated in the sample 18a. The manufacturing process was then readjusted, in a step-wise control fashion, back to the nominal fully adhered sample state. The amplitudes of the interface reflection peak and rear surface 44a reflection peak were monitored and the Adhesion Factor calculated in Error! Reference source not found.

Figure 5:
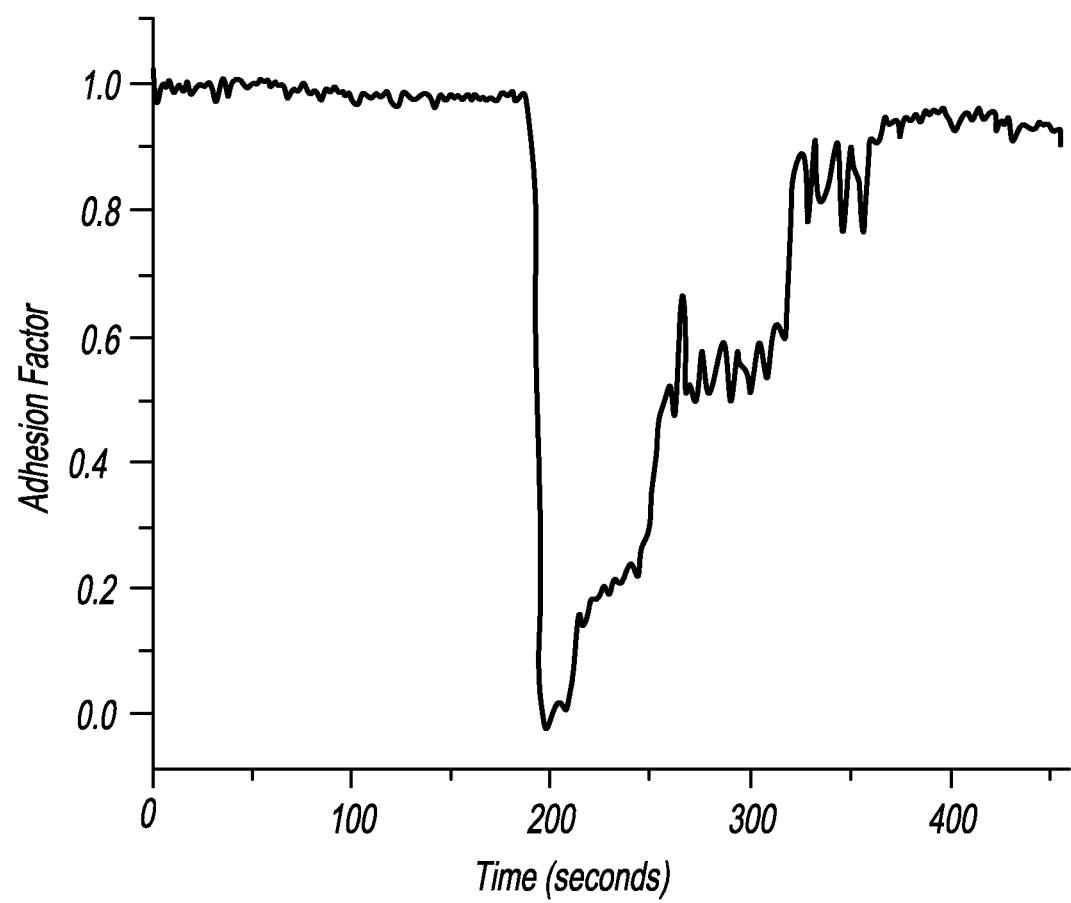
FIG. 5 illustrates the amplitudes of the interface reflection peak and rear surface reflection peak of a sample.

In FIG. 5, the normal operation of the well adhered sample 18a can be observed until the approximately 185 second time mark. At that point the manufacturing process is purposefully misadjusted to create a fully separated delamination type defect. The manufacturing process is then adjusted, in steps, to bring the process back into control. The final state is the full adhesion product being manufactured again. The Adhesion Factor, calculated from the interfacial reflection amplitude measurements, reveals this behavior. The immediate jump to zero adhesion is seen at 185 seconds, when the multilayer material separates in the individual layers. A series of sample property states are then observed:

| PRODUCT STATE | PERSISTENCE |
| --- | --- |
| Normal well adhered operation | 185 seconds (0 → 185 seconds) |
| Fully Delaminated | 30 seconds (185 → 215 seconds) |
| Extremely low adhesion/Delaminated | 28 seconds (215 → 243 seconds) |
| Transition region | 15 seconds (243 → 258 seconds) |
| Medium adhesion | 59 seconds (258 → 317 seconds) |
| Transition region | 8 seconds (317 → 325 seconds) |
| High adhesion (but still not nominal) | 40 seconds (325 → 365 seconds) |
| Return to normal production | (365 seconds onward) |

The sample property states correspond to the actions taken during the trial; the immediate appearance of a fully separated product and subsequent adjustment, in steps, to bring the manufacturing process back to nominal stable operation.

This measurement result was also proportional to other off-line physical measurements of adhesion (e.g., pull strength). Thus, this factor could be calibrated to measure such parameters on-line without contact. The example presented here considered adhesion at an interface but the invention promoted is not limited to such property measurements. Any process that affects an interface physical properties (e.g., curing of material at an interface) can be probed with the same system and method.

The above discussion considered inspection normal to the sample surface. The Fresnel equations, which describe the Reflection Coefficient at interfaces, do vary for the various polarization states of the electromagnetic radiation for off-axis measurements. The full Fresnel equations are:

$$R_s = \left[\frac{\sin(\theta_t - \theta_i)}{\sin(\theta_t + \theta_i)}\right]^2 =$$

$$\left(\frac{n_1 \cos\theta_i - n_2 \cos\theta_t}{n_1 \cos\theta_i + n_2 \cos\theta_t}\right)^2 = \left[\frac{n_1 \cos\theta_i - n_2\sqrt{1 - \left(\frac{n_1}{n_2}\sin\theta_i\right)^2}}{n_1 \cos\theta_i + n_2\sqrt{1 - \left(\frac{n_1}{n_2}\sin\theta_i\right)^2}}\right]^2$$

and $$R_p = \left[\frac{\tan(\theta_t - \theta_i)}{\tan(\theta_t + \theta_i)}\right]^2 =$$

$$\left(\frac{n_1 \cos\theta_t - n_2 \cos\theta_i}{n_1 \cos\theta_t + n_2 \cos\theta_i}\right)^2 = \left[\frac{n_1\sqrt{1 - \left(\frac{n_1}{n_2}\sin\theta_i\right)^2} - n_2 \cos\theta_i}{n_1\sqrt{1 - \left(\frac{n_1}{n_2}\sin\theta_i\right)^2} + n_2 \cos\theta_i}\right]^2$$

where $\theta_i$, $\theta_r$ and $\theta_t$ are the angles of the incident, reflected and transmitted rays respectively.

By varying the angle of inspection, the reflection coefficients will be affected. This capability could be employed to modify the amount of reflected power at interfaces between wide varying refractive index values and individual materials with very high or low index of refraction values. Making measurements while the sensor, or sample, varies in presentation angle would also provided additional information/confirmation of the results.

In the previous examples, the hardware and system described used singled sided reflection measurements. This measurement method allows the time and amplitude of the reflected pulses to be accurately determined. As was demonstrated, the amplitude of the reflected electromagnetic energy from the interface can be used to determine specific interfacial properties.

If the sample is multilayer, such as sample 18a, uncertainties in the source of the sample delay are possible. In reflection, the measured sample layer time delays can be due to either a thickness change or material/mass change (e.g., density) of one, or more, of the layers. Thus, in multilayer samples, the thickness/material properties often cannot isolated without some additional information about the sample. Single sided reflection measurements can provide some information regarding the individual layers, but again is insufficient without knowledge of other sample characteristics.

Figure 6:
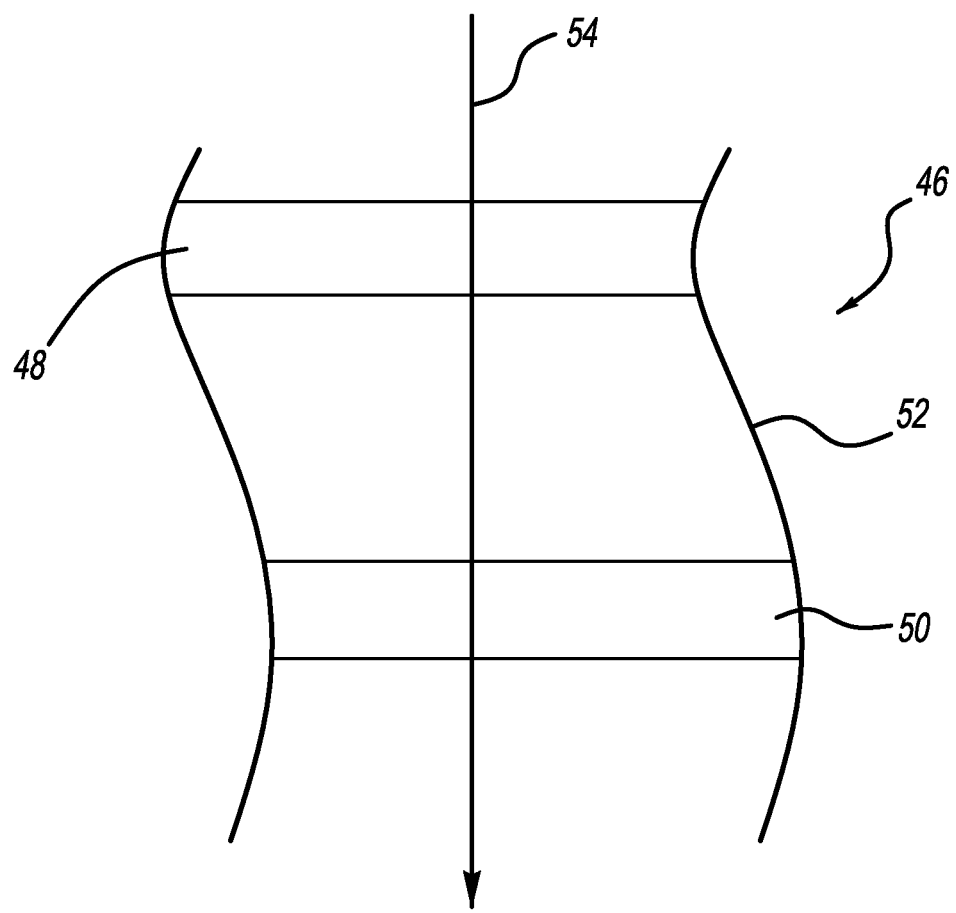
FIG. 6 illustrates a three layer sample.

Referring to FIG. 6, the simultaneous measurement of the sample transmission can reduce the number of sample properties that are needed to describe a sample 46. In this example, the top layer 48 and bottom layer 50 are the same material. Even if the thickness of the top and bottom layers 48 and 50 are know, the time delay of electromagnetic radiation 54 passing through the central layer 52 could be due to a thickness change or a material density change. If a simultaneous transmission measurement is also made, the time delay due to the central layer's 52 mass can be found with higher accuracy.

Of interest, for this example, is the delta time delay of central layer 52 material ($\Delta t_{L2}$). The overall sample thickness and the thickness of the outer covering layers 48 and 50 are known or assumed to be set values. Reflection measurements can precisely measure $\Delta t_{L2}$ (delta time-of-flight of central layer 52). However, as mentioned, there is not sufficient information to determine if variation in the $\Delta t_{L2}$ value is due to a layer thickness change or layer mass change or a layer density change.

If a transmission measurement is made, then the incongruity can be improved.

In transmission:

$$\Delta t_{Total} = \Delta t_{Sample} - \Delta t_{Air}$$

$$\Delta t_{Total} = \Delta t_{L1} + \Delta t_{L2} + \Delta t_{L3}$$

In reflection:

$$\Delta t_{L1} = \tfrac{1}{2}(t_2 - t_1 - d_{L1}/c) \quad d_{L1} = \text{thickness of Layer 1}$$

$$\Delta t_{L2} = \tfrac{1}{2}(t_3 - t_2 - d_{L2}/c) \quad d_{L2} = \text{thickness of Layer 2}$$

$$\Delta t_{L3} = \tfrac{1}{2}(t_4 - t_3 - d_{L3}/c) \quad d_{L3} = \text{thickness of Layer 3}$$

Assuming the layers 48 and 50 are the same thickness ($d_{Outer}$), then substituting the reflection equations into the equation for the $\Delta t_{Total}$ transmission and solving for $\Delta t_{L2}$ yields:

$$\Delta t_{L2} = \Delta t_{Total} + d_{Outer}/c - \tfrac{1}{2}(t_2 - t_1 + t_4 - t_3)$$

For reflection only measurements, the solution for $\Delta t_{L2}$ is:

$$\Delta t_{L2} = \tfrac{1}{2}(t_3 - t_2) - ((d_{Total} - 2d_{Outer})/c)$$

The added transmission measurement calculation method leads to improved accuracy of the $\Delta t_{L2}$ value because:

1) the transmission/reflection measurement is only sensitive to variations in $d_{Outer}$, as opposed to 2 $d_{Outer}$ in the reflection only measurement,
2) the reflection only measurement in sensitive to the $d_{Total}$ variation. The combination transmission/reflection measurements are not.

Once an improved accuracy value for $\Delta t_{L2}$ (i.e., delay due to the central layer 52 mass only) is known, then the layer thickness and density can be found. As has been previously described, the $d_{Total}$ value can be found with the hardware addition and method change to utilize an Internal Calibration Etalon structure around the sample. If the overall sample thickness is not known, then this hardware/method may be necessary. However, the invention described here does not require these additional components. If dual sided reflection measurements are made, the need for the Internal Calibration Etalon structure is eliminated.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A non-destructive method for determining a material property at an interface between a first layer and a second layer of a sample, the method comprising:
    outputting electromagnetic radiation to the sample;
    receiving electromagnetic radiation that was reflected by or transmitted through the sample, wherein the electromagnetic radiation received by the sample is non-destructive to the sample;
    digitizing the electromagnetic radiation reflected by or transmitted though the sample to yield waveform data, wherein the waveform data represents the electromagnetic radiation reflected by or transmitted though the sample, the waveform data having a first magnitude, a second magnitude and a third magnitude, wherein each magnitude is a peak or trough;
    wherein the first magnitude represents a reflected or transmitted portion of the electromagnetic radiation provided to a top surface interface of the first layer, the second magnitude represents a reflected or transmitted portion of the electromagnetic radiation provided to the interface between the first and second layers, and the third magnitude represents a reflected or transmitted portion of the electromagnetic radiation provided to a bottom surface interface of the second layer; and
    determining the material property between the first layer and the second layer of the sample by analyzing the second magnitude and/or the third magnitude;
    wherein the material property is adhesive strength; and
    determining the adhesive strength between the first layer and the second layer of the sample by analyzing the waveform data to determine if a fourth magnitude is located between the third magnitude and the second magnitude in time.

2. The method of claim 1, further comprising the step of determining the adhesive strength between the first layer and the second layer of the sample by comparing the second magnitude to a reference magnitude.

3. The method of claim 1, further comprising the step of determining the adhesive strength between the first layer and the second layer of the sample by comparing the third magnitude to a reference magnitude.

4. The method of claim 1, further comprising the step of determining the adhesive strength between the first layer and the second layer of the sample by comparing the third magnitude to the second magnitude.

5. The method of claim 1, wherein the electromagnetic radiation is terahertz radiation.

6. The method of claim 5, wherein the terahertz radiation is continuous wave terahertz radiation.

7. The method of claim 5, wherein the terahertz radiation is time-domain terahertz radiation.

8. The method of claim 5, wherein a frequency of the terahertz radiation is between 25 $GH_z$ to 10 $TH_z$.

9. The method of claim 1, further comprising the step of concluding that there is reduced adhesive strength between the first layer and the second layer when the fourth magnitude is located between the third magnitude and the second magnitude in time.

10. A non-destructive method for determining an adhesive strength at an interface between a first layer and a second layer of a sample, the method comprising:
    outputting electromagnetic radiation to the sample, wherein the electromagnetic radiation is non-destructive to the sample;
    receiving electromagnetic radiation that was reflected by or transmitted though the sample;
    digitizing the electromagnetic radiation reflected by or transmitted though the sample to yield waveform data, wherein the waveform data represents the electromagnetic radiation reflected by or transmitted though the sample, the a waveform data having a first magnitude, a second magnitude and a third magnitude, wherein each magnitude is a peak or trough;

wherein the first magnitude represents a reflected or transmitted portion of the electromagnetic radiation provided to a top surface interface of the first layer, the second magnitude represents a reflected or transmitted portion of the electromagnetic radiation provided to the interface between the first and second layers, and the third magnitude represents a reflected or transmitted portion of the electromagnetic radiation provided to a bottom surface interface of the second layer; and determining the adhesive strength between the first layer and the second layer of the sample by analyzing the waveform data to determine if a fourth magnitude is located between the third magnitude and the second magnitude in time.

11. The method of claim 10, further comprising the step of concluding that there is reduced adhesive strength between the first layer and the second layer when the fourth magnitude is located between the third magnitude and the second magnitude in time.

12. The method of claim 10, wherein the electromagnetic radiation is terahertz radiation.

13. The method of claim 12, wherein the terahertz radiation is continuous wave terahertz radiation.

14. The method of claim 12, wherein the terahertz radiation is time-domain wave terahertz radiation.

15. The method of claim 12, wherein a frequency of the terahertz radiation is between 25 $GH_z$ to 10 $TH_z$.

16. A non-destructive system for determining a material property at an interface between a first layer and a second layer of a sample, the system comprising:

a transmitter outputting electromagnetic radiation to the sample, wherein the electromagnetic radiation is non-destructive to the sample;

a receiver receiving electromagnetic radiation that was reflected by or transmitted though the sample;

a data acquisition device configured to digitize the electromagnetic radiation reflected by or transmitted though the sample to yield waveform data, wherein the waveform data represents the electromagnetic radiation reflected by or transmitted though the sample, the waveform data having a first magnitude, a second magnitude and a third magnitude, wherein each magnitude is a peak or trough;

wherein the first magnitude represents a reflected or transmitted portion of the electromagnetic radiation provided to a top surface interface of the first layer, the second magnitude represents a reflected or transmitted portion of the electromagnetic radiation provided to the interface between the first and second layers, and the third magnitude represents a reflected or transmitted portion of the electromagnetic radiation provided to a bottom surface interface of the second layer;

the data acquisition device configured to determine the material property between the first layer and the second layer of the sample by analyzing the second magnitude and/or the third magnitude; and the data acquisition device is further configured to determine an adhesive strength between the first layer and the second layer of the sample by analyzing the waveform data to determine if a fourth magnitude is located between the third magnitude and the second magnitude in time.

17. The system of claim 16, wherein the material property is adhesive strength.

18. The system of claim 17, wherein the data acquisition device is further configured to determine the adhesive strength between the first layer and the second layer of the sample by comparing the second magnitude to a reference magnitude.

19. The system of claim 17, wherein the data acquisition device is further configured to determine the adhesive strength between the first layer and the second layer of the sample by comparing the third magnitude to a reference magnitude.

20. The system of claim 17, wherein the data acquisition device is further configured to determine the adhesive strength between the first layer and the second layer of the sample by comparing the third magnitude to the second magnitude.

21. The system of claim 16, wherein the electromagnetic radiation is terahertz radiation.

22. The system of claim 21, wherein the terahertz radiation is continuous wave terahertz radiation.

23. The system of claim 21, wherein the terahertz radiation is time-domain terahertz radiation.

24. The system of claim 21, wherein a frequency of the terahertz radiation is between 25 $GH_z$ to 10 $TH_z$.

25. The system of claim 16, wherein the data acquisition device is further configured to determine that there is reduced adhesive strength between the first layer and the second layer when the fourth magnitude is located between the third magnitude and the second magnitude in time.

26. A non-destructive system for determining an adhesive strength at an interface between a first layer and a second layer of a sample, the system comprising:

a transmitter outputting electromagnetic radiation to the sample, wherein the electromagnetic radiation is non-destructive to the sample;

a receiver receiving electromagnetic radiation that was reflected by or transmitted though the sample;

a data acquisition device configured to digitize the electromagnetic radiation reflected by or transmitted though the sample to yield waveform data, wherein the waveform data represents the radiation reflected by or transmitted though the sample, the waveform data having a first magnitude, a second magnitude and a third magnitude, wherein each magnitude is a peak or trough;

wherein the first magnitude represents a reflected or transmitted portion of the electromagnetic radiation provided to a top surface interface of the first layer, the second magnitude represents a reflected or transmitted portion of the electromagnetic radiation provided to the interface between the first and second layers, and the third magnitude represents a reflected or transmitted portion of the electromagnetic radiation provided to a bottom surface interface of the second layer; and the data acquisition device configured to determine the adhesive strength between the first layer and the second layer of the sample by analyzing the waveform data to determine if a fourth magnitude is located between the third magnitude and the second magnitude in time.

27. The system of claim 26, wherein the data acquisition device is further configured to determine that there is reduced adhesive strength between the first layer and the second layer when the fourth magnitude is located between the third magnitude and the second magnitude in time.

28. The system of claim 26, wherein the electromagnetic radiation is terahertz radiation.

29. The system of claim 28, wherein the terahertz radiation is continuous wave terahertz radiation.

30. The system of claim 28, wherein the terahertz radiation is time-domain wave terahertz radiation.

31. The system of claim 28, wherein a frequency of the terahertz radiation is between 25 $GH_z$ to 10 $TH_z$.

* * * * *